United States Patent [19]

Hobbs et al.

[11] Patent Number: 4,873,355

[45] Date of Patent: Oct. 10, 1989

[54] PROCESS FOR REGIOSELECTIVELY PREPARING PHOSPHORYLATED INOSITOLS AND OTHER CYCLITOLS

[75] Inventors: Frank W. Hobbs; James L. Meek, both of Wilmington, Del.

[73] Assignee: E. I. Du Pont de Nemours and Company, Wilmington, Del.

[21] Appl. No.: 56,181

[22] Filed: May 29, 1987

[51] Int. Cl.$^4$ .............................................. C07F 9/117
[52] U.S. Cl. .................................. 558/161; 558/155
[58] Field of Search .............................. 558/155, 161

[56] References Cited

U.S. PATENT DOCUMENTS 4,755,612  7/1988  Vacca et al. ........................ 549/220

OTHER PUBLICATIONS

Majerus et al., Science, 234: 1519–1526 (1986).
Berridge, Scientific American, 253: 143–152 (1985).
Slotin, Synthesis, 737–752 (1977).
Billington et al., J. Chem. Soc. Chem. Commun., 314–316 (1987).
Krylova et al., J. Org. Chem. USSR, 16: 277–282 (1980).
Krylova et al., J. Org. Chem., 42: 697–702 (1972).
Vacca et al., J. Am. Chem. Soc., 109: 3478–3479 (1987).
Ozaki et al., Tetrahedron Lett., 28: 4691–4694 (1987).
deSolms et al., Tetrahedron Lett., 28: 4503–4506 (1987).
Billington et al., J. Chem. Soc. Chem. Comm. 1011–1013 (1987).
Cosgrove, J. Sci. Food Agric., 17: 550–554 (1966).
Angyal et al., J. Chem. Soc., 4122–4128 (1961).
Angyal et al., Aust. J. Chem., 22: 391–404 (1969).
Ozaki et al., Tetrahedron Lett., 27: 3157–3160 (1986).
Gigg et al., Carbohydrate Res., 140: c1–c3 (1985).
Letsinger et al., J. Amer. Chem. Soc., 98: 3655–3661 (1976).
Beaucage et al., Tetrahedron Lett., 22: 1859–1862 (1981).
Garegg et al., Chem. Scripta, 25: 280–282 (1985).
Takaku et al., Tetrahedron Lett., 411–414 (1972).
Gibbs et al., Synthesis, 410–413 (1984).
Horn et al., Tetrahedon Lett., 27: 4705–4708 (1986).
Uhlmann et al., Tetrahedron Lett., 27: 1023–1026 (1986).
Perich et al., Tetrahedron Lett., 28: 101–102 (1987).
Connolly, Tetrahedron Lett., 28: 463–466 (1987).
Hayakawa et al., Tetrahedron Lett., 28: 2259–2262 (1987).
Bannworth et al., Helv. Chim. Acta, 70: 175–186 (1987).
Kozlova et al., J. Gen. Chem. USSR, 39: 2403–2406 (1969).
Cooke et al., Tetrahedron Lett., 28: 2305–2308 (1987).
Reese et al., Tetrahedron Lett., 28: 2309–2312 (1987).
Hamblin et al., J. Chem. Soc. Chem. Comm., 626–627 (1987).
Dreef et al., Recl. Trav. Chim. Pays-Bas, 106: 161–162 (1987).

*Primary Examiner*—Anton H. Sutto

[57] ABSTRACT

A process for regioselectively preparing phosphorylated cyclitols, in particular phosphorylated inositols such as myo-inositol 1,4,5-tris(phosphate) and myo-inositol 1,3,4,5-tetrakis(phosphate). Novel cyclitols produced by means of this process are also described.

37 Claims, No Drawings

PROCESS FOR REGIOSELECTIVELY PREPARING PHOSPHORYLATED INOSITOLS AND OTHER CYCLITOLS

BACKGROUND OF THE INVENTION

1. Field of the Invention

The present invention discloses a process for regioselectively preparing phosphorylated cyclitols, in particular phosphorylated inositols such as myo-inositol 1,4,5-tris(phosphate) and myo-inositol 1,3,4,5-tetrakis (phosphate). Novel cyclitols produced by means of this process are also described.

2. Background of the Invention

Cyclitols are cycloalkanes containing one hydroxyl group on each of three or more ring carbons. The most abundant members of the cyclitol family are the inositols (1,2,3,4,5,6-hexahydroxycyclohexanes) and the most important stereoisomer of this family is myo-inositol which has the 1-, 2-, 3-, and 5-hydroxyl groups on one side of the ring and the 4- and 6-hydroxyl groups on the other. Phosphorylated derivatives of cylitols and inositols, that is, those which have one or more hydroxyl groups converted to phosphate monoesters, are generally referred to, respectively, as cyclitol phosphates or inositol phosphates.

Cellular processes of all animals, including man, depend, at least in part, upon inositol phosphates. Certain inositol phosphates function as "second messengers", that is, molecules which provide the means by which neurotransmitters, growth factors or hormones alter processes inside cells without necessarily penetrating the cells they affect. When the circulating hormone vasopressin binds to receptors on liver cells, for example, it stimulates an increase in intracellular concentrations of D-myo-inositol 1,4,5-tris(phosphate) and D-myo-inositol 1,3,4,5-tetrakis(phosphate). The increased concentrations of these second messengers in turn activates certain enzymatic processes within the cells. Similarly, some growth factors such as platelet derived growth factor (PDGF) cause increased production of inositol phosphates in the cells they affect. Intracellular concentrations of inositol phosphates also appear to play a role in the regulation of cell division and the inflammatory response. Because of the potential medicinal importance of the natural inositol phosphates, and analogs and isomers thereof, considerable research interest in these compounds has been generated. The National Library of Medicine's MEDLINE TM lists more than 1400 published papers since 1980 on the subject of inositol phosphates. Recent reviews can be found in Science, 234: 1519 (1986) and Scientific American, 253: 142 (1985).

Studies of inositol phosphates have been hindered by the limited amounts of material which are tediously isolated from natural sources. Practical synthetic routes for preparing significant amounts of these compounds or their analogs or isomers are not currently available. Research efforts would benefit greatly from the availability of adequate quantities of isomerically-pure synthetic materials. An object of the present invention is to provide a synthetic process for the efficient preparation of naturally occuring inositol phosphates and analogs and isomers thereof.

The broad steps utilized in art processes to synthesize phosphorylated cylitols such as inositols are as follows. First, an inositol compound having appropriately protected hydroxyl groups is obtained (Step 1). Next, the free hydroxyl groups in these precursors are converted to phosphate groups (Step 2), and finally, the hydroxyl protecting groups are removed (Step 3). In practice, the second step frequently consists of the following two stages: Step 2a, formation of a phosphorus-oxygen bond between the phosphorus of a "phosphorylating agent" (a compound where the phosphorus is in the $+5$ oxidation state ($P(+5)$)), and one or more inositol oxygens; and Step 2b, removal of any protecting groups which are on the phosphorylating agent, hereafter referred to as phosphorus protecting groups. The crucial element in the synthesis of these compounds is the phosphorylation step (Step 2a) and the agents which effect it. For a general review of phosphorylation see Slotin, Synthesis, 737 (1977).

Three types of $P(+5)$ phosphorylating agents have generally been employed in Step 2a:

Type I $(RO)_2-P(=O)-X$;

Type II $(RO)_2-P(=O)-OH$ or salt thereof; and

Type III $(RNH)_2-P(=O-X$ or $RCONH-P(=O)-(OH)(O^-)$; wherein R=phosphorus protecting groups and X=halogen.

The conversion of hydroxyl groups to phosphate monoesters generally has been accomplished by the action of a phosphorylating agent of Type I. One problem with most of the Type I agents is that phosphorylating agents which contain phosphorus($+5$) atoms are not sufficiently reactive to efficiently polyphosphorylate partially protected inositols. Monophosphorylation of 1,2,3,5,6-pentabenzylinositol with the classical phosphorylating agent, diphenyl chlorophosphate (Type I, wherein $R=C_6H_5$ and $X=Cl$), for example, affords only a 70% yield of the desired inositol diphenyl monophosphate (Billington et al., J. Chem. Soc., 314 (1987)). Polyphosphorylations, i.e., bis-, tris-, tetrakis-, etc., are difficult to acheive with selectivity, and separation of the many undesired phosphorylated side products from the desired phosphorylated product produced via this reaction scheme presents a difficult task. Forcing conditions, such as higher temperatures are problematic since these phosphorylating agents tend to decompose, as described in Krylova et al., J. Org. Chem. USSR, 16: 277-282 (1980), or effect premature removal of hydroxyl protecting groups, discussed in Krylova et al., Zh. Org. Khim., 42: 702 (1972).

The Type II phosphorylating agents are used in situ after having been converted to a mixed anhydride with an activating agent such as triisopropylbenzenesulfonyl chloride or dicyclohexylcarbodiimide. However, none of these reagents are any more reactive than the Type I reagents, and thus are equally inefficient at phosphorylating inositols. For example, inositol has been converted to a mixture of pentakis- and hexakis(phosphates) by heating in polyphosphoric acid at 120° C., as described by Cosgrove, J. Sci. Food Agric., 17: 550 (1966).

An equally significant disadvantage of the aforementioned Type I and Type II phosphorylating agents is that they have the potential to form cyclic phosphates when the substrate to be phosphorylated contains unprotected vicinal hydroxyl groups, especially cis vicinal hydroxyl groups. For example, when treated with diphenyl chlorophosphate, 1,2:5,6-di-O-isopropylidene-(-)-inositol (a trans vicinal diol) and 1,4,5,6-tetra-O-acetyl-myo-inositol (a cis vicinal diol) afford cyclic monophosphates instead of the desired 3,4- and 2,3-bis(phosphates) (Angyal et al., J. Chem. Soc., 4122 (1961)).

Although some bis(phosphates) can be prepared from the trans vicinal diols using diphenyl chlorophosphate, precautions must generally be taken with inositol phosphate triesters intermediates because they are exceptionally prone to cyclization onto a neighboring free hydroxyl group. For example, Billington et al., J Chem. Soc., 314 (1987find that 2,3,4,5,6-pentabenzyl-myo-inositol-1-(diphenyl phosphate) is deprotected by hydrogenolysis to a mixture of myo-inositol 1- and 2-phosphates. Migration of phosphate occurs because the benzyl ether protecting groups are removed more rapidly than the phosphorus protecting groups. Intermediate phosphate triesters with a free 2-hydroxyl group cyclize and then ring open to form the reported mixture of products.

The above cyclization and migration problems lead to the development of a third type of P(+5) phosphorylating agent, Type III, shown above. In this type of agent, one or two of the phosphorus oxygens are replaced by nitrogens. The phosphorylated products, i.e., inositol phosphoramidates or phosphorodiamidates, produced by this type of agent are apparently not as prone to cyclization as are the phosphorus triesters, probably because nitrogen is a poorer leaving group than oxygen. Angyal et al., Aust. J. Chem., 22: 391–404 (1969) reported obtaining a mixture of tetra- and the desired pentaphosphorylated products when attempting to exhaustively phosphorylate 1-O-benzyl-myo-inositol it with the monotriethylammonium salt of N-benzoyl-phosphoramidic acid in dimethylformamide (DMF) at 140° for 24 h. In this case, the phosphorus protecting groups (including removal of the nitrogen) and pyrophosphate intermediates were hydrolyzed with hydrochloric acid. Krylova, J. Org. Chem USSR, 16: 277 (1980), reports that phosphorylation of 1,2-O-cyclohexylidiene-3,6-di-O-benzyl-myo-inositol with "dianilidophosphoric chloride" afforded the desired 4,5-bis(phosphordiamidite). Dianilidophosphoric chloride appears to be about as reactive as the corresponding oxygen analog diphenyl phosphorochloridate. These nitrogen-containing phosphorus protecting groups can be removed by hydrolysis with aqueous hydrochloric acid or buffered nitrous acid. The former method has the potential to cause migration of phosphate groups and the highest yield reported for the latter method is 25%. These Type III phosphorylation agents, therefore, while offering hope of obtaining polyphosphates from a variety of protected inositols, have a number of unresolved problems associated with their use.

The first total synthesis of inositol 1,4,5-tris(phosphate) was reported by Ozaki et al., Tetrahedron Lett., 27: 3157–3160 (1986). This synthesis illustrates the weaknesses of the best existing technology when applied to a synthetically difficult, biologically important molecule. Ten steps of chemistry were required to prepare (+)-2,3,6-tri- benzylinositol, an appropriate precursor for phosphorylation. Tris(phosphorylation) was effected by means of dianilidochlorophosphate in "ca. 41% yield". The authors noted that "[a]t the present time, phosporylation and subsequent deblocking reaction[sic,reactions] [using isoamyl nitrite]are not satisfactory". No overall yield of final product was given. Gigg et al., Carbohydrate Res., 140: c1 (1985)) also reported a long synthesis of the same tribenzylinositol, but they have apparently been unable to obtain the desired tris(phosphate) from this precursor.

In conclusion, the regioselective synthesis of many inositol phosphates by means of the existing P(+5) technology is a long, risky and inefficient process.

Over the past decade, phosphorylation with phosphorus(+3) (P(+3)) phosphorylating agents (also known as phosphitylating agents) has revolutionized the field of oligonucleotide synthesis. First chlorophosphite diesters, developed by Letsinger et al., J. Am. Chem. Soc., 97: 3278 (1975), and then more recently phosphoramidites, developed by Beaucage et al., Tetrahedron Lett., 22: 1859 (1981), have been the reagents of choice for the construction of phosphorus diester, as opposed to monoester, bonds in oligonucleotides. The use of phosphorus(+3) reagents for the construction of phosphorus diesters requires that two key hydroxyl groups become attached to a monoprotected phosphitylating agent. Adapting phosphorus(+3) methodology to the preparation of phosphorus monoesters requires that one key hydroxyl group become attached to a phosphitylating agent with two protecting groups.

There are scattered reports in the literature on methods for preparing phosphate monoesters by means of phosphitylation agents. Many of these reports, however, involve the use of phosphitylating agents designed for making phosphate diesters and one would anticipate that these agents would produce cyclic phosphite esters from many inositol substrates. Bannwarth et al., Helv. Chim. Acta, 70: 175–186 (1987), report a comprehensive study on appropriate phosphitylating agents for making phosphate monoesters. Kozlova et al., J. Gen. Chem. USSR, 39: 2403–2406 (1969), disclose the only example of phosphitylation of a cyclitol derivative. These authors, however, were interested in the preparation of phosphate diesters of inositol, that is, phospholipids. Consequently, the phosphitylating agent they chose to use (the mixed anhydride from O-benzylphosphorous acid and O,O-diphenylphosphoric acid) is one which might be anticipated to produce cyclic phosphite esters with many of the inositol substrates of interest to this invention. Since all of the other hydroxyl groups in the inositol substrate they used were protected, they observed no cyclization and obtained an inositol (mono-) phosphite diester as the major product. No phosphite triesters of inositol are known.

The present invention centers around the creation of a superior process that uses phosphitylation as a key step in the preparation of cyclitol phosphates, particularly inositol phosphates. Prior to the studies disclosed herein, no one had used phosphitylation to prepare cyclitol phosphate monoesters nor had anyone used phosphitylation to attach more than one phosphorus to cyclitols. The general usefulness of phosphitylation for the preparation of poly(phosphates) from starting materials with more than one hydroxyl group did not appear to have been established. In particular, there was no evidence demonstrating that changing to methods based on phosphitylation would alleviate the side reactions which interfere with more conventional phosphorylating agents, i.e., incomplete poly(phosphorylation), cyclization, and phosphate migration.

Although the phosphitylating agents used in the present process have been employed in other systems, they have never been applied to the problem of producing inositol phosphates and other cyclitol phosphates, and indeed, their ability to effectively work in the present system and avoid many of the problems prevalent in the art processes is quite suprising.

SUMMARY OF THE INVENTION

The present invention involves a process for regioselectively producing cyclitol phosphates comprising reacting an optionally protected cyclitol with, in order of (a) through (c), (a) a bis-protected phosphitylating agent, (b) an oxidizing agent, and (c) a phosphorus deprotecting agent, and, if necessary (as is usually the case), a hydroxyl deprotecting agent. The preferred process produces an inositol phosphate, most preferably a myo-inositol poly(phosphate) such as the 1,3,4,5-tetrakis(phosphate) and the 1,4,5-tris(phosphate).

DETAILED DESCRIPTION OF THE INVENTION

The chemical process of this invention is directed primarily towards the synthesis of certain isomers of myo-inositol poly(phosphates), but this process is applicable to the regioselective synthesis of all inositol phosphates and more generally to the regioselective synthesis of any cyclitol phosphate. For simplicity sake, the methodology of this invention is illustrated in detail only for myo-inositol poly(phosphates).

The overall process of the present invention as illustrated by Scheme I relies on a superior, three-step method for phosphorylation, i.e., (a) phosphitylation followed by (b) oxidation, and then by (c) deprotection. In certain circumstances, it may be desirable to add an additional step, hydroxyl group protection, following step (a) and prior to step (b).

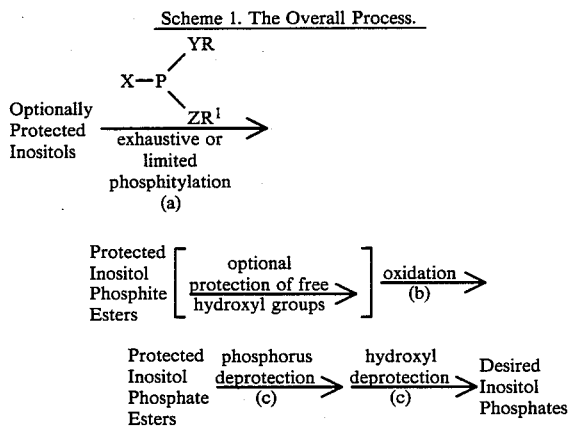

It should be noted that in conventional nomenclature, the three adjacent syn hydroxyl groups of myo-inositol are always designated as occupying the 1, 2, and 3 positions. Since myo-inositol possesses a plane of symmetry (i.e., it is a meso isomer), the 1 and 3 positions and the 4 and 6 positions are identical. When one of these positions is modified, two enantiomers are possible and the nomenclature for these compounds can become confusing. For example, the name 1(R)-myoinositol phosphate represents the same molecule as 3(S)-myo-inositol phosphate. Thus, for clarity, all synthetic intermediates are referred to herein by the numbering system of the desired final product. The IUPAC-approved name (European J. Biochemistry, 5: 1–12 (1968)), if different from the aforementioned nomenclature, will also be provided using brackets {☐}. As an example of the numbering system employed herein, an intermediate in the synthesis of myo-inositol 1,2,4,5-tetrakis(phosphate) with benzoates at the positions that will eventually become the 3- and 6-hydroxyl groups shall always be referred to as a 3,6-dibenzoate. The IUPAC nomenclature {1,4-dibenzoate} will appear as appropriate.

Throughout the specification, the term "phosphitylation" is defined as a reaction between a free hydroxyl group on a cyclitol, or more particularly an inositol compound, and a bis-protected electrophilic phosphorus species which has a phosphorus in the (+3) oxidation state, $P(+3)$, termed a "phosphitylating agent". The product of this process is a cyclitol or inositol phosphite ester, having a $P(+3)$ phosphorus group. Phosphitylation followed by oxidation results in a net "phosphorylation", which means that the phosphorus in the phosphorylated compound is converted to the (+5) oxidation state, $P(+5)$, as part of a phosphate monoester group.

As used herein "cyclitol phosphates" or "inositol phosphates" denote those phosphorylated derivatives of cyclitols or inositols which have one or more hydroxyl groups converted to phosphate monoesters. A cyclitol polyphosphate or inositol polyphosphate has more than one hydroxyl group converted to phosphate monoesters.

Phosphitylation is used in the process of the present invention for "regioselectively" preparing inositol phosphates. The term "regioselectively" denotes that a preselected number of phosphorus groups are attached to preselected oxygens of inositol. In accordance with the invention, regioselectivity is achieved by one or both of the following means: (i) selecting an inositol starting material which has protecting groups on all oxygens which are not phosphorylated in the desired final product, that is, those oxygens in the final product that are hydroxyl groups and not phosphate monoesters, or (ii) by limiting the phosphitylating reaction by reducing the amount of phosphitylating agent, the reaction time, the reaction temperature or any combinations thereof. The latter means (ii) of achieving regioselectivity is herein referred to as "limited" phosphitylation. Limited phosphitylation takes advantage of the intrinsic differences in reactivity of the inositol oxygens, particularly the lower intrinsic reactivity of the 2-position hydroxyl oxygen. In contrast, when regioselectivity is achieved by means (i), an excess of phosphitylating agent is used for a period long enough to completely phosphitylate all of the unprotected hydroxyl groups. In this case, the term "exhaustive" phosphitylation is employed herein.

One or more hydroxyl groups on the starting material may, as is usually desired, be "protected" by one or more "protecting groups", and the term "protected hydroxyl group" indicates this type of protected species. During phosphitylation reactions of the type described herein, protected hydroxyl groups do not react with the phosphitylating agent. The concept of using protecting groups to mask reactive functional groups is well understood in the field of synthetic chemistry and is discussed at length, for example, in Green, Protective Groups in Organic Synthesis, John Wiley & Sons, N.Y. (1981).

Which starting material hydroxyl groups should be protected depends upon the ultimate product desired. The concept that one skilled in the art can prepare an inositol starting material with the appropriate number (0 to 5) and types of protecting groups located on preselected hydroxyl groups is denoted by the terminology "optionally protected". As part of this invention, it has also been discovered that in the case where the hydroxyl group in the 2-position and several other hydroxyl groups are unprotected, the lower reactivity of the 2-hydroxyl group can be taken advantage of to obtain regioselectively phosphitylated products.

Suitable protecting groups for the hydroxyl groups of the cyclitol compounds include, but are not limited to, ethers, silyl ethers, esters, orthoesters, carbonates, cyclic acetals, cyclic ketals, cyclic orthoesters, and cyclic carbonates. Preferred protecting groups include benzyl ethers, benzoate esters and cyclohexylidene ketals.

Phosphitylation, the first and key step in the present process, is carried out by a phosphitylating agent. The phosphitylating agents used herein are "protected" by two "protecting groups", and the term "bis-protected phosphitylating agent" denotes such as species. Protecting groups on the phosphorus species are referred to herein as "phosphorus protecting group(s)".

Phosphitylating agents suitable for the present invention include, but are not limited to, compounds of the formula

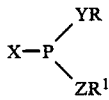

wherein
X is selected from the group consisting of
a halogen, i.e., F, Cl, Br or I,
$NR_2^2$, where $R^2$ is aryl or a $C_1$-$C_{15}$
straight chain, branched or cyclic alkyl where the alkyl may be internally interrupted by ether oxygen, and
OH or a salt thereof;
Y and Z, independently, are selected from the group consisting of
O
S,
NH, and
$NR^2$;
R and $R^1$, independently, are phosphorus protecting groups. Suitable phosphorus protecting groups include, but are not limited to,
aryl, and
a $C_1$-$C_{15}$ straight chain, branched or cyclic alkyl,
where the alkyl may be internally interrupted with ether oxygen and where aryl or the alkyl may be substituted or unsubstituted with nitro, sulfonyl, halogen ester and ketone groups; provided that
when Y or Z, singley or in combination, are O, then the group attached to O, that is, R and $R^1$, must be $CH_3$, $CH_2CCl_3$, aryl, $CH_2$—aryl, $CR_2^2CCl_3$, $CR_2^2CBr_3$, $CH_2CH_2$—A, wherein A is a group which will stabilize an adjacent carbanion such as a nitrile, a sulfonyl, or an electron-deficient aryl group such as p-nitrophenyl. Other suitable phosphorus protecting groups are known in the art.

In the above formula, X is preferably a halogen or $NR_2^2$. When X is a halogen, most preferably it is Cl. When X is $NR_2^2$, most preferably it is diisopropylamino or 1-morpholino group. Y and Z in the formula are preferably both O and when Y and Z are both O, R and $R^1$ are preferably both $CH_3$. The most preferred phosphitylating agent of the above formula is dimethyl chlorophosphite, that is where X is Cl, Y and Z are both O, and R and $R^1$ are both $CH_3$.

When the phosphitylating agent is a phosphoramidite (i.e., X is $NR_2$), a weak acid such as tetrazole is added to activate the agent. When the phosphitylating agent is a phosphorous acid diester (i.e., X is OH) or a salt thereof, the agent must be activated by a reagent capable of converting the phosphorus acid to a mixed anhydride. Examples of such reagents are triisopropylbenzenesulfonyl chloride and dicyclohexylcarbodiimide.

When the phosphitylating agent is a halophosphite or a phosphorous acid, about 1.0 to 2.0 equivalents of an acid scavenger per equivalent of phosphitylating agent is preferably added. In other cases an acid scavenger is optional. The preferred acid scavengers are low molecular weight, non-nucleophilic, tertiary amines. The most preferred acid scavenger is diisopropylethylamine. Heterocyclic amines such as pyridine and N-methylimidazole are used to catalyze reactions similar to phosphitylation. These heterocyclic amines can also be used in the phosphitylation reactions of this invention.

The phosphitylating agents described above are used to effect exhaustive or limited phosphitylation of optionally protected inositols. An inert solvent is employed in the reaction. Suitable solvents include halocarbons, ethers, esters, and polar aprotic solvents such as dimethylformamide, acetonitrile, pyridine and dimethylsulfoxide. It should be noted that a suitable solvent does not have to be one that has the ability to completely dissolve the inositol starting material, but it is preferably one which affords a homogeneous reaction mixture at some point during the phosphitylation reaction.

In the case of exhaustive phosphitylation to produce phosphite esters, the quantity of phosphitylating agent and the reaction conditions are adjusted so that no unprotected hydroxyl groups remain unphosphitylated when the reaction is halted. Exhaustive phosphitylation is effected by adding 1.0 to about 2.5 equivalents of phosphitylating agent per unprotected hydroxyl group. The phosphitylation can be performed at about −80 to 50° and for about 5 min to 24 h. Preferred reaction conditions are about 0 to about 20° for about 1h. The preferred solvents include dichloromethane. Dichloromethane is generally the most preferred solvent because removal of water soluble by-products is easier when the reaction is complete. However, when the optionally protected inositol starting materials are unusually insoluble, dimethylformamide is the most preferred solvent.

In the case of limited phosphitylation to produce phosphite esters, either or both the quantity of phosphitylating agent and the reaction conditions are adjusted so that some of the unprotected hydroxyl groups remain unphosphitylated when the reaction is halted. This is usually done by limiting the amount of phosphitylating agent to about 1.0 to 1.2 equivalents per hydroxyl group to be phosphitylated. The phosphitylating agent is preferably added to a solution of this precursor at about −70 to about −40°. The reaction is allowed to proceed within this temperature range for about 1 to about 24 h and then the reaction is slowly warmed to about 0°. For limited phosphitylation, the solvent preferably employed is able to completely dissolve the optionally protected inositol precursor. The preferred solvent is dimethylformamide. In the preferred version of limited phosphitylation, the unreacted hydroxyl groups are protected in situ with a hydroxyl protecting group before oxidation. Protection of the unreacted hydroxyl groups ensures that the phosphorus groups regioselectively introduced during limited phosphitylation do not migrate to neighboring free hydroxyl groups later in the synthesis. If this hydroxyl protecting step is omitted, inositol poly(phosphates) with lower isomeric purity will be produced. The preferred hydroxyl protecting groups used are esters, most preferably an acetate. Protection of the hydroxyl groups via esterification is preferably performed with an acid chloride in the presence of a catalyst. The most preferred catalyst is dimethylaminopyridine.

In the situation where one desires to phosphorylate all of the unprotected hydroxyl groups in an inositol compound except for an unprotected 2-hydroxyl group, the limited phosphorylation process described herein has been found to be surprisingly regioselective. Example 2, Step 1, describes a reaction in which three of four possible hydroxyl groups are phosphitylated. After oxidation, the only products detected are the desired tris(phosphate) and 5-10% of tetrakis(phosphate).

Following either exhaustive or limited phosphitylation the resulting phosphite esters are preferably not isolated. Oxidation to phosphate esters is performed with oxidizing agents such as peroxides, periodate, halogens and other halogenating agents (in the presence of water), oxygen, permanganate, chromate, iodobenzene diacetate, ozone, hypohalites, persulfate, ruthenium tetraoxide, etc. The most preferred oxidizing agents are hydrogen peroxide and meta-chloroperoxybenzoic acid. These oxidants are preferably used at about 0° to about 20°, preferably after adding a neutral aqueous buffer to quench any excess phosphitylating agent. The resulting phosphate esters are isolated by allowing (or causing, by addition of a poor solvent) them to precipitate from the reaction mixture. Alternatively, partitioning between aqueous and organic solvent affords a crude product which is optionally purified by chromatography or crystallization.

The protecting groups on the hydroxyl groups and the phosphorus groups are subsequently removed by, respectively, standard "hydroxyl deprotecting agents" and "phosphorus deprotecting agents". The preferred order of deprotection involves selective phosphorus deprotection followed by hydroxyl group deprotection. Reversing the order of deprotection, or simultaneous deprotection, is possible, but not usually preferred since the intermediate phosphate esters can cyclize. When this happens, the product will generally be an isomeric mixture of inositol poly(phosphates).

Suitable hydroxyl and phosphorus deprotecting agents will be readily apparent to those skilled in the art and exemplary agents are discussed below.

With respect to phosphorus deprotecting agents, in the situation where Y and/or Z of the phosphitylating agents are sulfur, for example, the phosphorus protecting groups are removed by oxidative hydrolysis, such as with iodine in the presence of aqueous buffer as described by Takaku et al., Tetrahedron Lett., 411–414 (1972).

Where Y and/or Z are $NR^2$, the phosphorus protecting groups can be removed with aqueous mineral acid. When Y and/or Z are NH, either mineral acid or buffered nitrous acid can be used. In either case, when phosphorus is still in the +3 oxidation state, these labile nitrogen protecting groups can be easily converted to phosphite esters by treatment with an acid and an alcohol respectively.

Finally, in the situation where Y and/or Z are O, the suitable phosphorus protecting groups depend upon the nature of R and $R^1$. Table I, below, provides some examples of phosphorus deprotecting agents.

TABLE I

| R and $R^1$ | Phosphate Deprotecting Agents |
|---|---|
| $-CH_3$ | [TMSBr or HBr] |
| $-CH_2-CBr_3$ | [Zn/HOAc] |
| $-CH_2-CCl_3$ | [Zn/HOAc] |
| -Aryl | [$H_2$, Pd/C] |
| $-CH_2$—Aryl | [$H_2$, Pd/C] |
| -9-fluorenylmethyl | [$NH_4OH$] |
| $-CH_2-CH_2-Q$, | [DBU] | wherein Q is a group which will stabilize an adjacent carbanion such as a nitrile, sulfonyl, or an electron-deficient aryl group (i.e. p-nitrophenyl).

Methyl protecting groups on the most preferred phosphitylating agent, dimethyl chlorophosphite (Y and Z are O, and R and $R^1$ are $CH_3$), are preferrably removed with bromotrimethylsilane in an inert solvent such as dichloromethane or hydrobromic acid in anhydrous acetic acid. Other reagents which can remove these methyl esters include: other anhydrous acids with nucleophilic conjugate bases (such as hydroiodic acid), oxygenophilic Lewis acids with nucleophilic ligands (such as iodotrimethylsilane and boron tribromide), and hard Lewis acids in the presence of soft nucleophiles (such as boron trifluoride/propanethiol). When an acid-labile hydroxyl protecting group such as cyclohexylidene is present, bromotrimethylsilane is the most preferred agent, since it is the most chemoselective. A second advantage of bromotrimethylsilane is that deprotection with this reagent is actually a two step process. First, treatment of an inositol poly(dimethyl phosphate) with this reagent initially produces an inositol poly(bis(trimethylsilyl)phosphate) and this intermediate spontaeously hydrolyzes to a deprotected phosphate monoester on contact with water. Other deprotection methods frequently generate inositol poly(dihydrogen phosphates) which (as moderately strong acids) may be unstable. A third advantage of bromotrimethylsilane is that if premature deprotection of hydroxyl protecting group(s) has occurred, this reagent will temporarily protect them as silyl ethers. When the hydroxyl protecting groups are benzoates, premature removal of these protecting groups is not a problem and hydrobromic acid is the most preferred agent for its convenience. After removal of either of these volatile reagents the resulting inositol poly(dihydrogen phosphates) can be isolated by precipitation as a salt or simply used directly in the next reaction. It should be noted that standard methods (i.e., aqueous ammonia used in oligonucleotide synthesis) for removing the methyl protecting groups from phosphorus will not work here.

A more complete discussion of phosphorus deprotection can be found in Sonveaux, Bioorganic Chemistry, 14: 274–325 (1986) and the references discussed therein.

As noted above, the hydroxyl protecting groups, which include those present in the optionally protected inositol starting materials and any hydroxyl protecting groups added in the limited phosphorylation process, are generally removed last. Suitable hydroxyl deprotecting agents include aqueous hydroxide, most preferably aqueous potassium hydroxide. Green, "Protective Groups in Organic Synthesis", John Wiley & Sons, N.Y. (1981) provides other examples of suitable hydroxyl deprotecting agents.

The Examples that follow contain procedures for preparing two novel optionally protected inositol starting materials, 3,6-dibenzoyl-myo-inositol and 2,6-dibenzoyl-myo-inositol, which are useful, respectively, for preparing the naturally occuring second messengers myo-inositol 1,4,5-tris(phosphate) and myo-inositol 1,3,4,5-tetrakis(phosphate). Schemes 4 and 3, respectively, depict the synthesis process of these compounds. The preparation of two isomers of these natural compounds, myo-inositol 1,2,4,5 tetrakis(phosphate) myo-inositol 1,4,5,6 tetrakis(phosphate), is also described in the Examples. Schemes 2 and 5, respectively, depict the synthesis process of these compounds. Many of the other optionally protected inositols and other cyclitols contemplated as starting materials in the present process are obtainable through known synthesis procedures.

Scheme 2.
Synthesis of Myo-Inositol 1,2,4,5-Tetrakis(phosphate) (6).

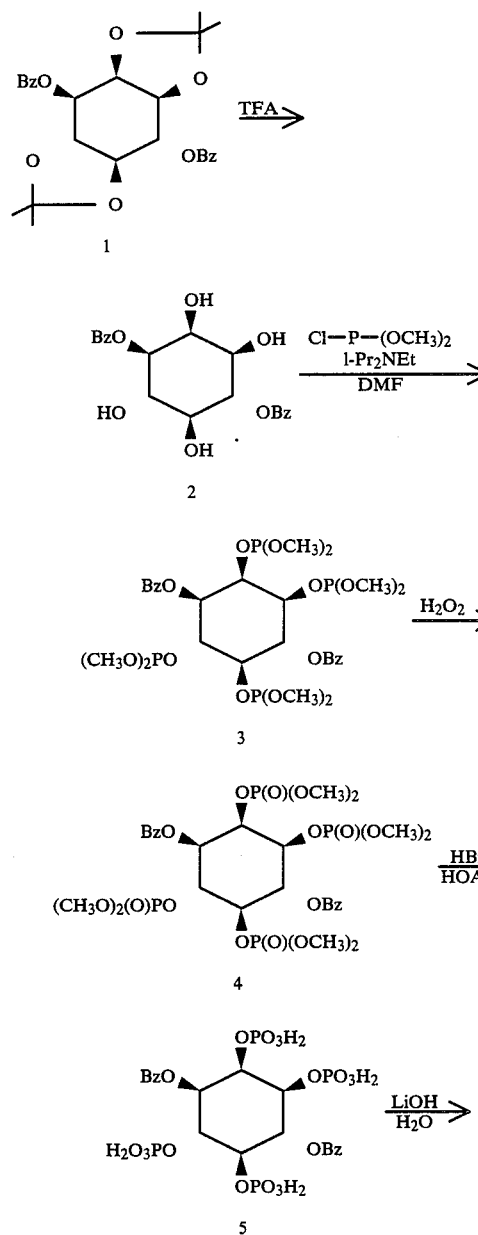

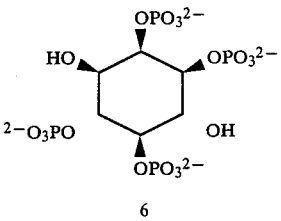

Scheme 3.
Synthesis of Myo-Inositol 1,3,4,5-Tetrakis(phosphate) (11).

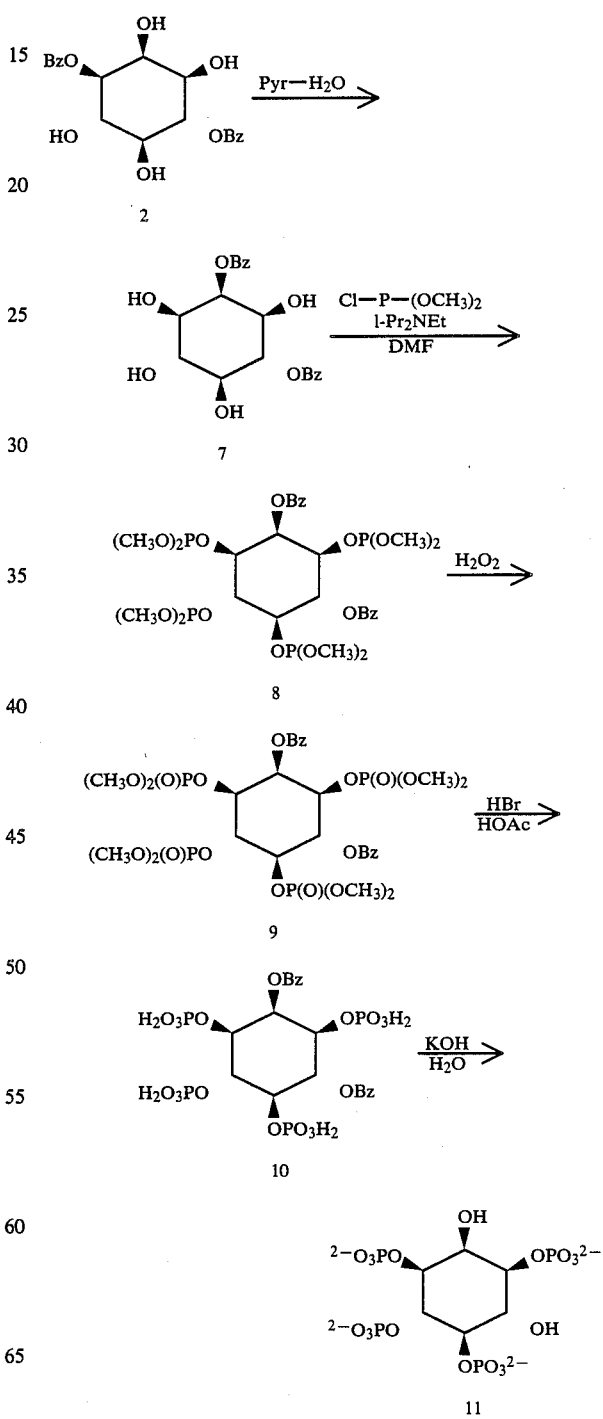

Scheme 4. Synthesis of Myo-Inositol 1,4,5-Tris(phosphate) (15).

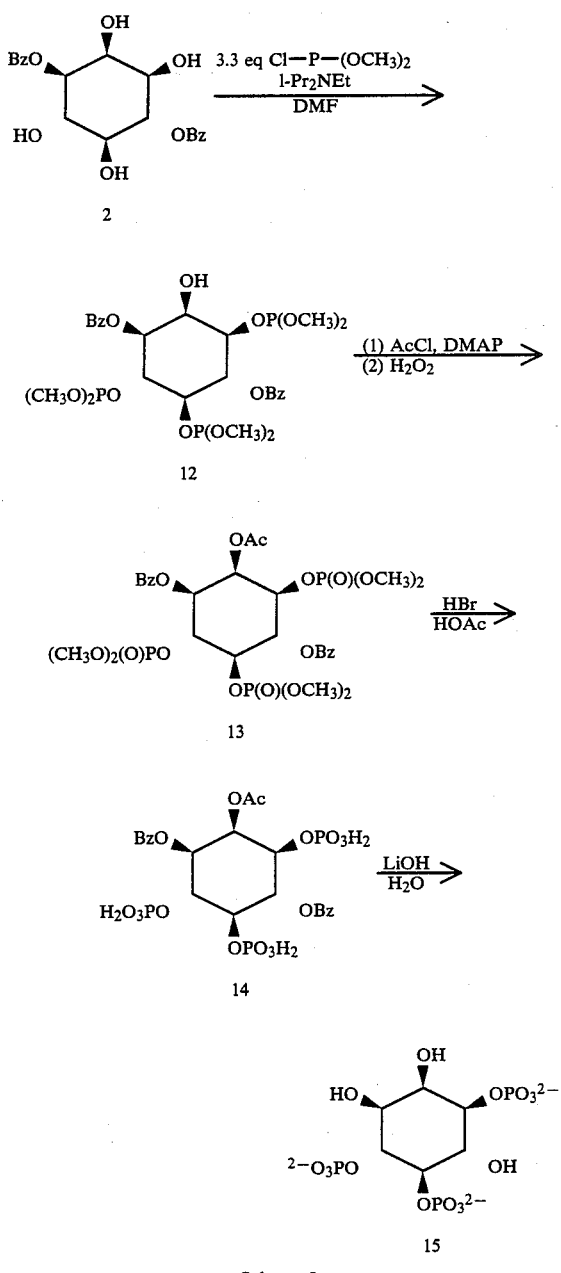

Scheme 5.
Synthesis of Myo-Inositol 1,4,5,6-Tetrakis(phosphate) (27).

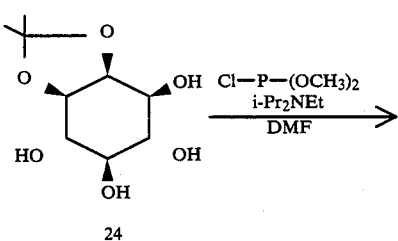

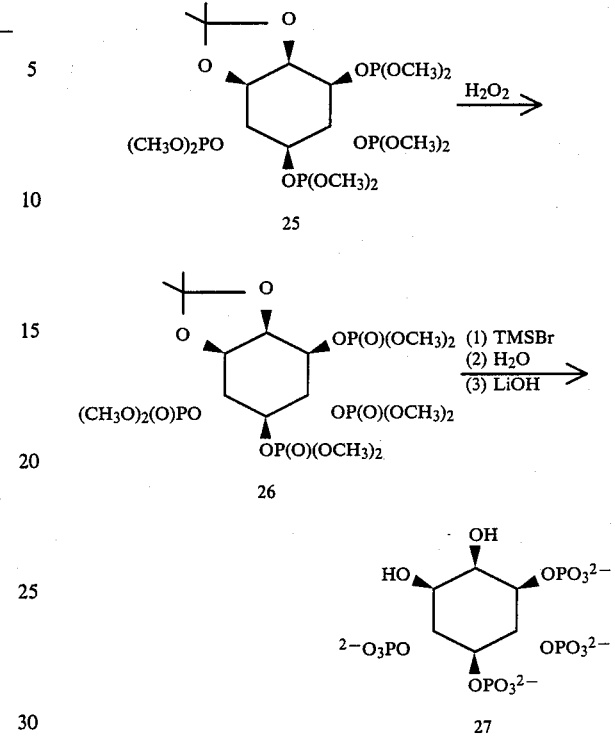

The list of compounds given below in Table II includes a few additional available starting materials organized by final product which may be obtained therefrom in accordance with the present invention. This list is not intended to be all inclusive.

TABLE II

| Product (inositol phoshate) | Inositol Derivative | Reference |
|---|---|---|
| 1,2,3,4,5,6-hexakis- | (inositol) | |
| 1,2,3,4,5-pentakis- | 6-benzyl- {4-benzyl-} | A |
| 1,2,4,5,6-pentakis- | 3-benzyl- {1-benzyl-} | A |
| 1,2,3,4,6-pentakis- | 5-benzyl- | A |
| 1,2,4-tris- | 3,6-diallyl-5-benzyl- {1,4,-diallyl-5-benzyl-} | B |
| 1,2,5-tris- | 3,6-diallyl-4-benzyl- {1,4,-diallyl-6-benzyl-} | B |
| 1,2-bis- | 1,4,5,6-tetrabenzyl- | C |
| 1,4-bis- | 2,3:5,6-diisopropylidene- {1,2:4,5-diisopropylidene-} | D |
| 1,6-bis- | 2,3:4,5-dicyclohexylidene- {1,2,5,6-dicyclohexylidene-} | E |
| 4,5-bis- | 1,2:3,4-dicyclohexylidene- | E |

References

A. Garegg et al., Carbohydrate Res., 130: 322 (1984).
B. Gigg et al., Carbohydrate Res., 140 c1–3 (1985).
C. Angyal et al., J. Chem. Soc., 6949 (1965).
D. Gigg et al., Carbohydrate Res., 142: 132–134 (1985).
E. Angyal et al., J. Chem. Soc., 4116 (1961).

Optionally protected starting materials suitable for the preparation of all of the 63 possible isomers (including enantiomers) of myo-inositol mono- and poly(phosphates) are available using conventional synthetic techniques. For example, an inositol starting material with all six hydroxyl groups differentiated might be prepared as described below and shown in Scheme 6. Both enantiomers of 4-O-benzyl1,6:2,3-di-O-cyclohexylidene-myo-inositol are first prepared in pure form as described by Garegg et al., Carbohydrate Res., 139: 209–215 (1985). The remaining 5-hydroxyl can be protected and the less stable, trans-fused 1,6-ketal can be selectively hydrolyzed. (Angyal et al., J. Chem. Soc., 4116 (1961) describe a similar selective hydrolysis. Klyashchitskii et al., Zh. Org. Khim., 7 : 492 (1971) report that in inositol derivatives similar to diol 18 differentiation between the 1- and 6-hydroxyl groups is possible since the 1-hydroxyl group is hindered by being on the endo face of this cis-fused ring system. Once the 1 and 6 positions are differentiated, the remaining ketal can be removed. The axial 2-hydroxyl group is known to be much less reactive than any of the other hydroxyl groups, thus these hydroxyl groups in diol 21 can also be differentiated. For this process protecting groups $R^a$ through R, can be either: permanent hydroxyl protecting groups or temporary hydroxyl protecting groups. In this context, "temporary" protecting groups are those which are removed prior to phosphitylation whereas "permanent" protecting groups remain. The synthesis of 2,3,6-tribenzylinositol as reported in Osaki et al., Tetrahedron Lett., 27: 3157–3160 (1986) was carried out using a similar strategy. While the above route generally will not be the most efficient one for preparing an optionally protected inositol, this route demonstrates that synthesis of appropriate starting materials for any myo-inositol phosphate is possible.

Scheme 6. Differentially Protecting Inositol Hydroxyl Groups.

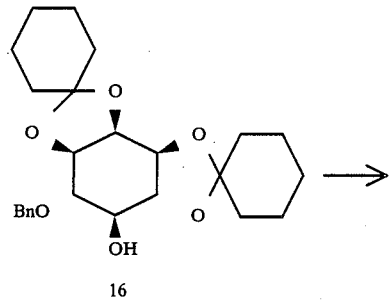

16

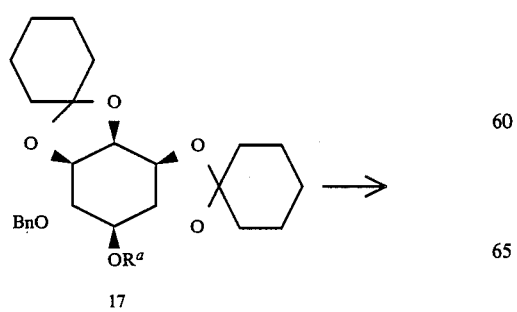

17

-continued
Scheme 6. Differentially Protecting Inositol Hydroxyl Groups.

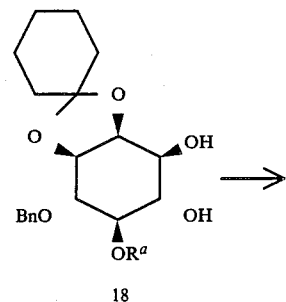

18

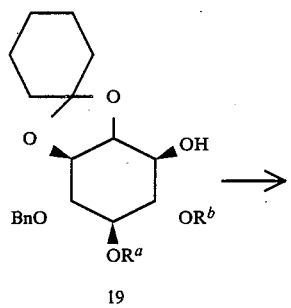

19

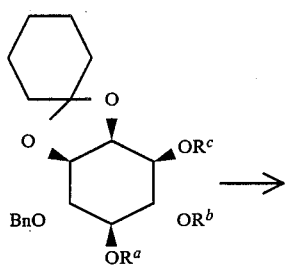

20

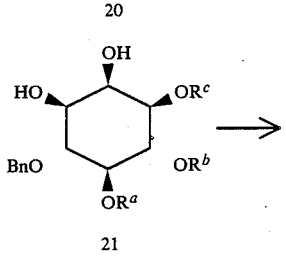

21

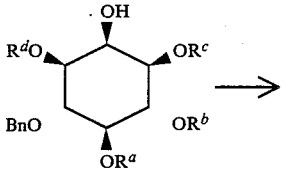

22

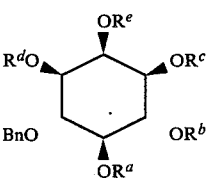

23

As part of this invention, a novel and convient method was developed for preparing starting materials suitable for the synthesis of the biologically important molecule myo-inositol 1,3,4,5-tetrakis (phosphate). An optionally protected inositol starting material for the above synthesis has protecting groups on the 2- and 6-hydroxyl groups {2- and 4-hydroxyl groups}. Since the hydroxyl groups of inositol are most easily differentiated by means of cyclic ketals, such starting materials are not readily available and indeed have never been reported. One object of this invention is a convenient process for the preparation of 2,6-diacylated inositols {2,4-diacylated inositols}. The known 2,3:4,5- {1,2:5,6-}and 1,2:4,5-bisketals of inositol, reported by Garegg, Carbohydrate Res., 130: 322 (1984) and Gigg et al., Carbohydrate Res., 142: 132 (1985), are acylated and the ketal groups are hydrolyzed. The resulting 1,6- or 3,6{1,4}-diacylinositol is isomerized by means of a basic catalyst to a mixture 1,6-, 2,6- {2,4}, and 3,6- {1,4} diacylinositol. Acyl groups preferred for this process are those which hydrolyze slowly and the substrate preferred is 3,6-{1,4}dibenzoylinositol. Acyl migration is effected by means of a basic catalyst such as a tertiary amine (e.g., triethylamine), sodium hydroxide, potassium t-butoxide, sodium hydride, or sodium acetate. The preferred catalysts are non-nucleophilic (e.g., tertiary amine, potassium t-butoxide or sodium hydride). The more preferred catalysts are weakly-basic (e.g., pyridine or sodium acetate). The most preferred catalyst is pyridine. A solvent containing some water is preferred and aqueous pyridine is the most preferred solvent. A reaction time and temperature compatible with the concentration and strength of the basic catalyst is used. In the most preferred reaction medium (6:4 pyridine-water), the reaction is performed at temperatures from about 0° to 100° and for times of about 10 min to 20 days. Reaction for 1 h at 100° is the most preferred. The mixture of isomers can be separated by a precipitation, fractional crystallization, and/or chromatography. The most preferred method is to add water or an alcohol to the most preferred reaction mixture to precipitate the 3,6-dibenzoate {1,4-dibenzoate} and then isolate the 2,6-dibenzoate {2,4-dibenzoate} by fractional crystallization from a second solvent such as dichloromethane or water.

The practicality of the above process is surprising for several reasons. First, separation of these three isomers is remarkably easy. Second, the review of the chemistry of myo-inositol by Shvets, Russian Chem. Rev., 43: 488 (1974)) states on page 492 that acetyl migration "is almost equally probable in trans- and cis- directions." This implies that the basic conditions needed to generate the desired 2,6-{2,4} isomer should produce all 15 possible diacyl isomers.

The methods disclosed herein provide a novel and superior process for regioselectively preparing inositol phosphates. In particular, these methods, which are based on phosphitylating agents, have the following advantages over conventional P(+5) phosphorylating agents. First, phosphitylating agents are intrinsically more reactive than phosphorylating agents. Phosphitylation followed by oxidation therefore generally affords higher yields of purer products than direct phosphorylation, especially when more than one phosphorus is attached to an inositol. Second, the preferred phosphitylating agents show no tendency to produce cyclic phosphites. Third, using this process, phosphorus migration can be avoided. Finally, limited phosphitylation appears to be more regioselective and useful than limited phosphorylation, and use of limited phosphitylation can greatly simplify the preparation of optionally protected inositol starting materials for synthesis of inositol phosphates which lack a 2-phosphate group.

Many of the intermediates prepared by the process described herein have never been synthesized before. For instance, no examples of inositol phosphites, inositol tris(phosphates), and inositol tetrakis(phosphates) in which all phosphorus groups are esterified have been reported. Aside from their utility as intermediates for the preparation of inositol phosphates, these families of compounds could serve as medicinally useful prodrugs. Intracellular hydrolysis of the esters which block the phosphate groups would result in release of the naturally-occurring inositol phosphate second messengers or analogs thereof.

By means of the process of this invention, suitable quantities of cylitol phosphates, especially myo-inositol phosphates, can be prepared in isomerically-pure form. Synthetically prepared, naturally occuring inositol phosphates and analogs and isomers thereof can be used in research on biological and medicinal phenomena associated with these second messengers. In particular, compounds prepared by means of this invention can be used as starting materials for the preparation of radioactively-labeled inositol phosphates. For example, Angyal et al., Aust. J. Chem., 20: 2647–2653 (1967) describe a method for tritiating inositols using tritiated water and a platinum oxide catalyst. The isomers and analogs of the natural second messengers made available by means of the present invention are candidates as agonists and antagonists.

General Methods

Unless otherwise stated, all inositol derivatives are racemates. Unless otherwise stated, all parts and percentages are by weight and all temperatures are in degrees Celsius. Compounds in the Examples are referred to by underlined numbers.

NMR spectra were obtained on GE 300 MHz or Bruker 360 MHz instruments. Unless otherwise stated, spectra were determined in deuterochloroform and chemical shifts were calculated relative to internal tetramethyl silane. Spectra of aqueous samples were referred to water set at 4.80 ppm. Coupling constants (J) are reported in Hz.

Thin Layer Chromatography (TLC) was carried out on 2.5×7.5 cm silica gel plates with fluorescent binder (Whatman, Maidstone, England). Solvent A=85:15:1 chloroform-methanol-water (volume/volume) was used.

1,2:4,5-Diisopropylidene-3,6-dibenzoyl- myo-inositol (1) and 3,4-isopropylidene myo-inositol (24) were prepared as described by Gigg et al., Carbohydrate Research, 142: 132 (1985). Dimethyl chlorophosphite was prepared as described by Mazour, U.S. Pat. No. 4,079,103 (1978).

High Pressure Liquid Chromatography (HPLC) was performed on a Mono Q (Pharmacia, Uppsala) anion exchange column. Buffer "A" contained 50 mM HEPES and was at pH 7.4; Buffer "B" contained 250 mM sodium sulfate and 10 mM HEPES, and was at pH 7.4. Both buffers also contained 1 mM $MgSO_4$, 0.1 mM $ZnSO_4$ and 0.1 mM EDTA. A gradient of 5 % B to 90% B in 30 min was used. The flow rate was 1 mL/min. Detection was by absorbance at 240 nm (inositol benzoates) or the on-line enzymatic system for detection of phosphomonoesters of Meek, Proc. Natl. Acad. Sci., 83: 4162, (1986).

EXAMPLE 1—PREPARATION OF LITHIUM MYO-INOSITOL—1,2,4,5TETRAKIS(PHOSPHATE) (6)

Step 1. Preparation of 3,6-dibenzoyl-myo-inositol {1,4-dibenzoyl-myo-inositol} (2)

A solution of 20 g (42.3 mmol) of bisacetonide 1 in 300 mL of boiling chloroform was hydrolysed by the addition of 30 mL trifluoroacetic acid and 3 mL of water. The mixture was refluxed until the reaction was complete according to TLC (about 30 min). Product began to precipitate after 5 min. After the mixture had cooled, collecting and drying the precipitate gave 11.8 g (71% yield) of dibenzoate 2 as a white powder melting at 243°–246°.

TLC (Solvent A): 1 Rf=0.95; 2, 0.55; 1,2-isopropylidene-3,6-dibenzoyl inositol, 0.75. $^1$H NMR (DMSO-d6) $\delta$=7.5-8.1 (m, 10H, benzoate), 5.3 (t, J =10, 1H , H6), 5.1 (m, 4H, 4 OH), 4.8 (dd, J =2,10, 1H, H3), 4.1 (s, 1H, H2), 3.9 (t, J =10, 1H, H 4 or5), 3.7 (dd, J =2,10, 1H, H1), 3.5 (t, J =9, 1H ,H4 or 5)

Step 2. Preparation of 3,6-dibenzoyl-myo-inositol 1,2,4,5-tetrakis(dimethyl phosphate) (4)

A 100-mL round-bottomed flask with septum cap and magnetic stirrer bar was charged with 3.00 g (7.7 mmol) of dibenzoate 2, 12 mL of dry dimethylformamide, and 14 mL (80 mmol, 10.4 eq) of dry diisopropylethylamine (Aldrich, Milwaukee, Wis.; distilled from calcium hydride). Dimethyl chlorophosphite (7.6 mL, 70 mmol, 9.1 eq) was added slowly at room temperature. After 15 min the mixture was cooled on ice and 12 mL of 0.5 M pH 7 sodium phosphate buffer and 12 mL (about 100 mmol, 14 eq) of 30% hydrogen peroxide were added. After standing overnight at 0°, the resulting precipitate was collected, washed with water, air dried, and washed with ether to give 4.2 g, (73% yield) of tetrakis(phosphate) 4 as a crystalline powder. TLC (Solvent A): Rf=0.66. H1-decoupled $^{31}$P NMR: $\delta$=1.68, 2.03, 2.17 and 2.74 ppm. $^1$H-NMR $\delta$7.2–7.8 ppm (m, 10 H benzoate), 5.9 (t, 1H, H2); 5.2–5.4 (m,3H); 4.9 (m, 2H); 3.2–4.8 (m 24H, OCH$_3$). Material from a similar preparation melted at 211–213°.

Step 3. Preparation of lithium 3,6-dibenzoyl-myoinositol 1,2,4,5-tetrakis(phosphate) (5)

A solution of 2.20 g (2.68 mmol) of tetrakis(dimethyl phosphate) 4 in 20 mL of 30% hydrogen bromide in acetic acid (Aldrich) was heated at 60° for 0.5 h. The reaction mixture was concentrated on a rotary evaporator (at about 1 mm, 40°) and the residue was co-evaporated twice with water. The residue was dissolved in water, and the pH of the resulting solution was adjusted to 10 with 4M aqueous lithium hydroxide. The basic reaction mixture was added dropwise with vigorous stirring to ethanol. After standing at 0° for 1 h, the resulting precipitate was filtered, and washed with ethanol and ether to yield 1.70 g of the lithium salt of tetrakis(phosphate) 5. HPLC: With detection by UV at 240 nm, there was only a single peak. It had a retention time of 24 min which indicated a tetrakis(phosphate). There was no detector response with the enzymatic phosphate monoester detection system.

Step 4. Preparation of lithium myo-inositol-1,2,4,5-tetrakis(phosphate) (6)

A solution of 1.80 g (2.40 mmol) of dibenzoate 5 (from a preparation similar to step 3 above) in 5.1 mL of 1.0M aqueous lithium hydroxide was heated at 60° for 1 h. HPLC of the reaction mixture showed the complete disappearance of the UV peak due to 5, and the appearance (using enzymatic phosphate detection) of a 9:1 mixture of two peaks with appropriate retention times for tetrakis- and tris(phosphates) respectively. The pH of the mixture was adjusted to 5 with 1.0M hydrochloric acid. The reaction mixture was adsorbed to a 2.5 cm by 25 cm Dowex 1 column, and the products were eluted with a lithium chloride gradient Three 10 mL fractions of each of the following concentrations of lithium chloride were collected: 0.1, 0.2, 0.3. 0.4, 0.5, 0.6, 0.7 and 0.8M. The effluent fractions were checked by isocratic HPLC using a mobile phase of 85 % "B" buffer. Fractions from the second 0.5M fraction to the third 0.7M lithium chloride fraction contained only the desired tetrakis(phosphate) and were combined and evaporated to near dryness The residue was triturated with ethanol to produce a powder. The powder was collected by filtration, and washed with ethanol and ether to give 0.50 g of tetrakis(phosphate) 6. HPLC, $^1$H-NMR and $^{31}$P-NMR indicated that this material was homogeneous. Gradient HPLC using phosphate detection showed a single peak with a retention time of 24.1 min $^1$H-decoupled $^{31}$P NMR (pH 10) $\delta$=6.17, 6.29, 6.35, and 6.64. $^1$H NMR (pH 10) $\delta$=4.5 (d, 1H H2), 4.15 (app q, J=9, 1H, H4) 3.7–3.9 (m, 3H, H1, H5, H6) 3.5 (dd, J=2,13, 1H, H3).

EXAMPLE 2. PREPARATION OF LITHIUM MYO-INOSITOL 1,4,5-TRIS(PHOSPHATE) (15)

Step 1. Preparation of 2-acetyl-3,6-dibenzoyl-myoinositol 1,4,5-tris(dimethyl phosphate) (13)

A 50-mL, three necked flask fitted with septum cap, internal thermometer and magnetic stirrer bar was charged with 1.00 g (2.6 mmol) of 3,6-dibenzoylinositol (2), 10 mL of dry dimethylformamide and 2.6 mL (15 mmol, 5.8 eq) of dry diisopropylethylamine. After cooling to −40°, 0.93 mL (8.6 mmol, 3.3 eq) of dimethyl chlorophosphite was added dropwise so that the temperature remained below −40°. After 30 min at −40°, the reaction was allowed to slowly warm to room temperature. Then 25 mg (0.33 mmol, 0.13 eq) of 4-dimethylaminopyridine (Aldrich) and 0.35 mL (4.9 mmol, 1.9 eq) of acetyl chloride were added. After stirring for 30 min at room temperature, 3 mL (about 26 mmol, 10 eq) of 30 % hydrogen peroxide was added dropwise. The reaction mixture was allowed to stand overnight at 0° . The resulting precipitate was collected, washed with water, and vacuum dried to yield 1.19 g (61%) of impure tris(dimethyl phosphate) 13. According to TLC, the desired product was contaminated with 5–10% of tetrakis(dimethyl phosphate) 4. Impure material from several similar preparations (1.6 g) was recrystallized by dissolving in 20 mL of acetone, and adding about 30 mL of water. After standing overnight at 0° , 0.8 g of crystalline product 13 was collected. This material melted at 224°–228° and was homogeneous by TLC and NMR. TLC (Solvent A): tris(phosphate) 13, Rf=0.73; tetrakis(phosphate) 4, 0.66; starting material 2, 0.55. $^1$H-decoupled $^{31}$P NMR $\delta$=2.55, 2.11 and 1.96. $^1$H-NMR $\delta$=7.6–8.2 (m, 10H ,benzoate), 5.9 (m, 2H) 5.15 (q, 1H), 4.8 (m, 3H), 3.2–3.8 (m, 18 H, OCH$_3$), 2.2 (s, 3H, Ac).

Step 2. Preparation of lithium myo-inositol 1,4,5-tris(phosphate) (15)

A solution of recrystallized tris(dimethyl phosphate) 13 (1.20 g, 1.60 mmol) in 10 mL of 30% hydrogen bromide in acetic acid was heated at 60° for 1 h. The reaction mixture was concentrated with a rotary evaporator (at about 1 mm and 40°). The residue was co-evaporated twice with water. The crude product was dissolved in water and the pH of the solution was adjusted to 10.3 by the addition of 4M aqueous lithium hydroxide. The basic solution was added with vigorous stirring to ethanol. The resulting mixture was allowed to stand for 1 h on ice, after which the precipitate was collected by filtration, and washed with ethanol and ether. A solution of the resulting intermediate dibenzoate 14 in 5 mL of 1 M lithium hydroxide was heated at 60° for 30 min. After cooling, the reaction mixture was added dropwise with stirring to ethanol. After 1 h, the resulting precipitate was collected by filtration and washed with ethanol and ether to give 640 mg of the product 15, as a white powder. Gradient HPLC using phosphate detection indicated that this precipitate was a 95:5 mixture of tris(phosphate) 15 (15.5 min) and inositol bis(phosphates) (8.13). $^1$H-NMR pH 10) $\delta=4.37$ (s, 1H, H2); 4.27 (app q, J =8.7, 1H, H4) 3.95–4.1 (m, 3H, H1,5,6): 3.83 (dd, J=2.5, 8.7, 1H, H3).

EXAMPLE 3. PREPARATION OF LITHIUM MYO-INOSITOL 1,3,4,5-TETRAKIS(PHOSPHATE) (11)

Step 1. Preparation of 2,6-dibenzoyl-myo-inositol {2,4-dibenzoyl-myo-inositol}(7)

To a solution of 11.6 g of 3,6-dibenzoate 2 (30 mmol) in 120 mL of pyridine at 100°° was added 80 mL water. While monitoring by TLC, the mixture was heated at 100°, until most of the 3,6 dibenzoate was converted to a mixture of 2,6 and 1,6 dibenzoates. After 2 h, the reaction was concentrated with a rotary evaporator and coevaporated twice with ethanol. The residue was triturated with ethanol and the ethanol extract was concentrated to about 5 mL and filtered. Acording to TLC (Solvent A), the ethanol extract was an approximately 20:10:1 mixture of 2,6-dibenzoate 7; 1,6-dibenzoate; 3,6-dibenzoate 2; and an unknown material. The residual solid was 5.8 g (50%) of 3,6-dibenzoate 2. Dichloromethane was added until the ethanol solution was turbid and the mixture was stored at 0° overnight. Collection of the resulting precipitate gave 1.10 g (10% yield) of 2,6-isomer 7.

TLC (solvent A) 2 Rf=0.55; unknown side product, 0.48; 7, 0.40; 1,6 dibenzoate, 0.28. NOTE: A sample of 1,6-dibenzoyl inositol was obtained by acid hydrolysis of 2,3:4,5-diisopropylidene-1,6-dibenzoyl inositol, a side product from the preparation of bisacetonide 1. $^1$H NMR of a similar preparation $\delta=5.5$ppm (s, 1H, H2), 5.3 (t, 1H, H6), 3.9 (dd, 1H, H1) 3.7 (m, 2H, H3,4); 3.5 (t, 1H, H5). When the signal at 5.3 ppm was irradiated, the signal at 3.9 (H1) collapsed to a s and that at 3.5 to a doublet (H5)

Step 2. Preparation of 2,6-dibenzoyl-myo-inositol 1,3,4,5-tetrakis(dimethyl phosphate) (9)

A 100-mL, round bottomed flask equipped with a magnetic stirrer bar and septum cap was charged with 1.20 g of 2,6-dibenzoate 7 (3.1 mmol), 20 mL of methylene chloride and 5.2 mL (30 mmol) of dry diisopropylethylamine. After cooling the mixture to 0° on ice, 2.6 mL (24 mmol) of dimethyl chlorophosphite was added during 2 min via syringe. The mixture was removed from the ice and the stirred for 30 min. The mixture was recooled to 0°, and 6 mL of 0.5 M sodium phosphate at pH 7.0 and 10 mL (about 88 mmol, 28 eq) of 30% hydrogen peroxide were added. The resulting two phase mixture was stirred vigorously for 10 min at 0° and then 1 h at 25°. The layers were separated and the organic layer was washed with phosphate buffer and water. After concentrating, the residue was dissolved in ether and allowed to crystallize overnight. The crystals were filtered off and washed with ether to produce 1.50 g of tetrakis(dimethyl phosphate) 9 as a white powder.

TLC (Solvent A) Rf=0.60. $^1$H-NMR (of material from a similar preparation) $\delta=7.4$–8.2 (m, 10H, benzoate); 6.2 (t, J =2.8, 1 H, H2); 5.9 (t, J=10.2, 1H, H6); 5.02 (app. q, J =b 9.7, H4); 4.84 (dt, J=2.7,10.2 1H, H4); 4.75 (app q, J =9.4, 1H, H5); 4.58 (dt, J =2.7, 10.2, 1H, H3). $^1$H-decoupled $^{31}$P-NMR $\delta=2.39, 2.35, 2.34, 1.64$ Step 3. Preparation of lithium myo-inositol 1,3,4,5-tetrakis(phosphate) (11)

A solution of 1.05 g (1.6 mmol) of tetrakis(dimethyl phosphate) 9 in 10 mL of 30% hydrogen bromide in acetic acid was heated at 60° for 30 min. The reaction mixture was concentrated with a rotary evaporator (at about 1 mm and 40°). The residue was co-evaporated twice with water. The residue was dissolved in water and the pH of the solution was adjusted to 10.0 with 1.0M aqueous potassium hydroxide. Gradient HPLC analysis showed that this solution contained a single UV-absorbing peak at 29 min, (10), and nothing that responded on the phosphate detection system. Addition of this solution to rapidly stirred ethanol gave a gum rather than a dry precipitate. The entire crude product was concentrated and heated with 3.8 mL of 1.0M aqueous potassium hydroxide at 80° for 1 h. After cooling, the solution was added dropwise with rapid stirring to ethanol. After standing at 0° for 1 h, the resulting precipitate was collected by filtration and washed with ethanol and ether to yield 850 mg of crude potassium salt 11. Gradient HPLC using phosphate detection showed that this material was a 95:5 mixture of tetrakis(phosphate) 11, (retention time 24 min) and tris(phosphates) (15 min), with no response on the UV detector at 240 nm. A portion (400 mg) of the crude precipitate was further purified by dissolving it in 20 mL water, adjusting the solution to pH 5 with Dowex 50 (H form), and adding the solution to a 1×13 cm column of Dowex 1×8 (100–200 mesh). Materials adsorbed on the column were eluted with 90 mL of a linear 0.0–0.6M lithium chloride gradient, at a rate of 1 mL/min. Tetrakis(phosphate) 11 was eluted and resolved from the other products. The appropriate fractions (63–78 ml) were combined, adjusted to pH 11.0 with 1.0M aqueous lithium hydroxide and evaporated to dryness. After thorough washing with ethanol (to remove lithium chloride), vacuum drying gave 102 mg of tetrakis(phosphate) 11.

$^1$H NMR of a similar preparation (DMSO+trifluoroacetic acid, 65°) $\delta=4.52$ (app. q, J=9.3, 1H, H4); 4.23 (s, 1H, H2), 4.23 (dt, J =2.5, 10.2, 1H, H3); 4.17 (app. q, J =8.9, 1H, H5); 4.02 (dt, J =2.5, 10.2, 1H, H1); 3.83 (t, J =11, 1H, H6). With decoupling of phosphorous, the signals at 4.52, 4.23 collapsed to triplets and the signal at 4.02 collapsed to a doublet of doublets, and changes are observed at 4.17. $^{31}$P-NMR (DMSO+trifluoroacetic acid, 65°) $\delta=1.015, 0.56, 0.42, 0.147$.

EXAMPLE 4. PREPARATION OF MYO-INOSITOL 1,4,5,6-TETRAKIS (PHOSPHATE) (27)

Step 1. Preparation of 2,3-isopropylidene-myo-inositol 1,4,5,6-tetrakis(dimethyl phosphate) (25)

A 100-mL, round bottomed flask equipped with a magnetic stirrer bar and septum cap was charged with 1.30 g (5 mmol) of 2,3-isopropylidene-myo-inositol 24, 15 mL of dry methylene chloride and 6.0 mL (34.5 mmol, 6.9 eq) of dry diisopropylethylamine. Dimethyl chlorophosphite (2.7 ml, 25.1 mmol, 5.0 eq) was added dropwise at 20°. The mixture was stirred for 30 min at 20°. After cooling to 0°, 12 mL of 0.5 M pH 7.0 phosphate buffer and 5 mL (about 43 mmol, 8.6 eq) of 30% hydrogen peroxide were added. After stirring vigorously for 30 min at room temperature, the phases were separated. The organic phase was washed twice with equal volumes of a saturated aqueous sodium chloride, and then concentrated on a rotary evaporator to give 2.5 g of an oily residue. TLC analysis (90:10:1 dichloromethane methanol-water) indicated that this material contained a major product, 25, (Rf=0.45) that was UV-inactive and acid charrable, and a minor unknown UV-active impurity (Rf=0.50). Material prepared in a similar fashion was apparently homogeneous by NMR. $^1$H NMR $\delta$=1.4,1.6 (s, 3H, CH$_3$); 3.8 (m, 24H, OCH3); 4.42 (t, J =7.5, 1H); 4.6-4.8 (m, 4H); 4.9 (m, 1H).

Step 2. Preparation of lithium myo-inositol 1,4,5,6tetrakis(phosphate) (27)

A 15-mL test tube with standard tapered joint was charged with 0.5 g (about 1 mmol) of acetonide 25, 0.5 mL of dry dichloromethane and 1.2 mL (9.1 mmol, 9.1 eq) of bromotrimethylsilane (Aldrich). After stirring for 30 min at 20°, solvent and by-products were removed by rotary evaporation. The oily residue was stirred with 1.0 mL of water for 1 h at 20° to hydrolyze the ketal and then evaporated to dryness. The residue was dissolved in 1 mL of water, and the pH of the resulting solution adjusted to 10.0 with 4.0M aqueous lithium hydroxide. This solution was added dropwise to 3 mL of ethanol. The resulting precipitate was collected and washed with ethanol and ether, giving 216 mg of tetrakis(phosphate) 27 as an amorphous powder. The product was redissolved in 2 mL of water and reprecipitated as above to give 140 mg of dried product 27. This material was homogenous by HPLC. HPLC: The product gave a single major peak (>95%) with the phosphate detection system with a retention time of 24 min, characteristic of a tetrakis(phosphate). H1-NMR of the free acid (i.e., prior to lithium hydroxide treatment) from a similar preparation (d6-DMSO), $\delta$=3.58 (dd, J =2,10, 1H, H3); 3.88 (broad s, 1H, H2); 4.47 (app q, J =10, 1H); 4.2–4.36 (m, 3H).

$^1$H NMR D$_2$O+d1−TFA, pH <2, 60°) $\delta$=4.90 (app. q, J =9.3); 4.78 (app. q, J =10); 4.68–4.58 (m); 4.62 (s, H2); 4.1 (dd, J =2.7,9.7, H3). With phosphorous decoupling, the signals at 4.9 and 4.78 collapsed to singlets. $^{31}$NMR (D$_2$O, pH 10, 55°) $\delta$=6.65, 6.40, 6.03, 5.72.

What is claimed is:

1. A myo-inositol poly(phosphate) of the formula

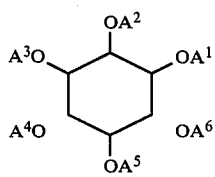

wherein
A$^1$ through A$^6$ are independently selected from the group consisting of
H,
a hydroxyl protecting group, and
P(=O)(YR)(ZR$^1$),
where
R and R$^1$ are, independently, a phosphorus protecting group,
Y and Z are, independently, selected from the group consisting of O, S, and NR$^2$, where R$^2$ is aryl or a C$_1$–C$_{15}$ staight chain, branched or cyclic alkyl where the alkyl may be internally interrupted by ether oxygen, provided that
three or four of A$^1$ through A$^6$ are P(=O)(YR)(ZR$^1$).

2. A myo-inositol poly(phosphate) according to claim 1, wherein the phosphorus protecting groups, R and R$^1$ are, independently, aryl, or a C$_1$–C$_{15}$ straight chain, branched or cyclic alkyl, where the alkyl may be internally interrupted with ether oxygen and where aryl or the alkyl may be substituted or unsubstituted with nitro, sulfonyl, halogen ester, and ketone groups.

3. A process for regioselectively producing a cyclitol phosphate comprising reacting an optionally protected cyclitol with, in order:
(a) a bis-protected phosphitylating agent;
(b) an oxidizing agent; and
(c) a phosphorus deprotecting agent, and if necessary, a hydroxyl deprotecting agent.

4. A process according to claim 3 wherein the cyclitol phosphates are inositol phosphates.

5. A process according to claim 4 wherein the inositol phosphates are myo-inositol phosphates.

6. A process according to claim 5 wherein the myo-inositol phosphates are myo-inositol poly(phosphates).

7. A process according to claim 6 wherein the myo-inositol poly(phosphates) are myo-inositol tris(phosphates).

8. A process according to claim 6 wherein the myo-inositol poly(phosphates) are myo-inositol tetra(phosphates).

9. A process according to claim 6 wherein the myo-inositol poly(phosphates) are selected from the group consisting of myo-inositol 1,2,4,5-tetrakis (phosphate), myo-inositol 1,4,5,6-tetrakis(phosphate), myo-inositol 1,4,5-tris(phosphate) and myo-inositol 1,3,4,5-tetrakis(phosphate).

10. A process according to claim 9 wherein the myo-inositol poly(phosphate) is myo-inositol 1,4,5-tris(phosphate).

11. A process according to claim 9 wherein the myo-inositol poly(phosphate) is myo-inositol 1,3,4,5-tetrakis(phosphate).

12. A process according to claim 4 wherein the protected phositylating agent is of the formula

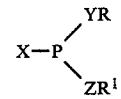

wherein
X is selected from the group consisting of
a halogen, NR$_2$$^2$, where R$^2$ is aryl or a C$_1$–C$_{15}$ straight chain, branched or cyclic alkyl where the alkyl may be internally interrupted by ether oxygen, and OH or a salt thereof;
Y and Z, independently, are selected from the group consisting of
O,
S,
NH, and NR$^2$;

R and R¹, independently, are phosphorous protecting groups selected from the group consisting of aryl, and a $C_1$–$C_{15}$ straight chain, branched or cyclic alkyl, where the alkyl may be internally interrupted with ether oxygen and where aryl or the alkyl may be substituted or unsubstituted with nitro, sulfonyl, halogen ester and ketone groups; provided that when Y or Z, singly or in combination, are O, then the group attached to O, that is, R and R¹, must be $CH_3$, $CH_2CCl_3$, $CH_2CBr_3$, aryl, $CH_2$–aryl, $CR_2{}^2CCl_3$, $CR_2{}^2CBr_3$, $CH_2CH_2$–Q, wherein Q is a group which will stabilize an adjacent carbanion such as nitrile, sulfonyl, or an electron-deficient aryl group such as p-nitrophenyl.

13. A process according to claim 12 wherein X is a halogen.

14. A process according to claim 13 wherein X is Cl.

15. A process according to claim 12 wherein X is $NR_2{}^2$.

16. A process according to claim 15 wherein $NR_2{}^2$ is diisopropylamino or 1-morpholinyl.

17. A process according to claim 12 wherein Y and Z are both O.

18. A process according to claim 17 wherein R and R¹ are both $CH_3$.

19. A process according to claim 12 wherein X is Cl, Y and Z are both O, and R and R¹ are each $CH_3$.

20. A process according to claim 4 wherein the phosphorus deprotecting agent is added first and the hydroxyl deprotecting agent is added second.

21. A process according to claim 4 wherein the optionally protected inositol is protected.

22. A process according to claim 4 wherein the reaction in step (a) is carried out with an excess quantity of phosphitylating agent.

23. A process according to claim 22 wherein the inositol phosphate is myo-inositol 1,3,4,5-tetrakis (phosphate).

24. A process according to claim 4 wherein the reaction in step (a) is carried out with a limited quantity of phosphitylating agent or for a limited amount of time or both.

25. A process according to claim 24 wherein the inositol phosphate produced has a free hydroxyl group in the 2-position.

26. A process according to claim 25 further comprising, prior to step (b), reacting the product of step (a) with a hydroxyl protecting agent.

27. A process according to claim 26 wherein the hydroxyl protecting agent is an acylating agent.

28. A process according to claim 27 wherein the inositol phosphate is myo-inositol 1,4,5-tris (phosphate).

29. A process for selectively producing a cyclitol phosphite ester comprising reacting an optionally protected cyclitol with a bis-protected phosphitylating agent.

30. A process according to claim 29 further comprising reacting the cyclitol phosphite ester with an oxidizing agent to yield a cyclitol phosphate ester.

31. A process according to claim 30 further comprising reacting the cyclitol phosphate ester with a phosphorous deprotecting agent to yield a cyclitol phosphate.

32. A process according to claim 30 wherein the cyclitol is protected and further comprising reacting the cyclitol phosphate ester with phosphorus and hydroxyl deprotecting agents to yield a cyclitol phosphate.

33. A process according to claim 32 wherein the cyclitol phosphate ester is first reacted with the phosphorus deprotecting agent and then secondly reacted with the hydroxyl deprotecting agent.

34. A process according to claim 29 wherein the amount of the protected phosphytilating agent is limited, and further comprising reacting the cyclitol phosphite ester with a hydroxyl protecting agent.

35. A process according to claim 34 further comprising reacting the cyclitol phosphite ester with an oxidizing agent to yield a cyclitol phosphate ester.

36. A process according to claim 35 further comprising reacting the cyclitol phosphate with phosphorus and hydroxy deprotecting agents to yield a cyclitol phosphate.

37. A process according to claim 36, wherein the cyclitol phosphate ester is first reacted with the phosphorus deprotecting agent and then secondly reacted with hydroxyl deprotecting agent.

* * * * *